United States Patent
Takahama

(10) Patent No.: US 8,101,346 B2
(45) Date of Patent: Jan. 24, 2012

(54) IDENTIFIER AND NUCLEIC ACID AMPLIFICATION METHOD OF VERIFICATION USING THE SAME

(75) Inventor: Shinichiro Takahama, Matsudo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1329 days.

(21) Appl. No.: 11/517,342

(22) Filed: Sep. 8, 2006

(65) Prior Publication Data

US 2007/0059750 A1 Mar. 15, 2007

(30) Foreign Application Priority Data

Sep. 13, 2005 (JP) ................................. 2005-266021

(51) Int. Cl.
*C12Q 1/68* (2006.01)
*C07H 21/04* (2006.01)
*C12M 1/34* (2006.01)
*G01N 33/48* (2006.01)

(52) U.S. Cl. ............ 435/6; 536/23.1; 536/24.1; 702/19; 702/20; 435/287.2

(58) Field of Classification Search .................. None
See application file for complete search history.

(56) References Cited

U.S. PATENT DOCUMENTS

| | | |
|---|---|---|
| 5,139,812 A | 8/1992 | Lebacq |
| 5,362,648 A | 11/1994 | Koreyasu et al. ............... 436/48 |
| 5,811,235 A | 9/1998 | Jeffreys ............................. 435/6 |
| 5,853,989 A | 12/1998 | Jeffreys et al. ................... 435/6 |
| 2004/0058374 A1 | 3/2004 | Shen et al. |

FOREIGN PATENT DOCUMENTS

| | | |
|---|---|---|
| EP | 0 530 009 | 3/1993 |
| JP | 5-288754 | 11/1993 |
| JP | 6-205700 | 7/1994 |
| JP | 2002-72536 A | 3/2002 |
| JP | 2002-72542 A | 3/2002 |
| JP | 2002-167530 A | 6/2002 |
| JP | 2004-159502 A | 6/2004 |

OTHER PUBLICATIONS

Shumaker et al., Human Mutation, 7:346-354, 1996.*
Nishida, et al., DNA Computing, vol. 5, No. 4, 2001, pp. 107-110, and p. 180.
Leier, et al., "Cryptography with DNA binary strands", BioSystems, vol. 57, 2000, pp. 13-22.
Nishida, et al., Gene Analysis by DNA Computing, vol. 5, No. 4, 2001, pp. 107-110.

* cited by examiner

*Primary Examiner* — Shubo Zhou
(74) *Attorney, Agent, or Firm* — Fitzpatrick, Cella, Harper & Scinto

(57) ABSTRACT

There is provided an identification technique that can consistently maintain a set of information specifying a specimen through all the processes from the amplification process to the detection process of a specific sequence. A base sequence incorporating as a set of decodable information an individual code imparted to the specimen is disposed in an amplifiable region to form an identifier; the identifier is amplified together with the specimen and the presence of the identifier in the amplification product is detected; thus, the individual code of the specimen in the amplification product can be recognized, which specimen the amplification product is derived from can be easily identified, and whether or not the amplification has been carried out satisfactorily can also be simultaneously tested.

11 Claims, 3 Drawing Sheets

S-PRIMER REGION   CODE REGION   A-PRIMER REGION

INDIVIDUAL SPECIMEN CODE
(DECODED DATA)

10111100100101

10 11 11 00 10 01 01
G  A  A  T  G  C  C

[INITIAL STATE]    [AMPLIFICATION PROCESS]

302    302 AFTER AMPLIFICATION 301    301 AFTER AMPLIFICATION

401

402

SEQUENCE LISTING

<160> NUMBER OF SEQ ID NOS: 4

<210> SEQ ID NO 1
<211> LENGTH: 178
<212> TYPE: DNA
<213> ORGANISM: Homo sapiens

<400> SEQUENCE: 1
ttggtagtga ggcaggtatg gggctagaag cactggtgcc cctggccgtg atagtggcca      60
tcttcctgct cctggtggac ctgatgcacc ggcgccaacg ctgggctgca cgctacycac     120
caggccccct gccactgccc gggctgggca acctgctgca tgtggacttc cagaacac      178

<210> SEQ ID NO 2
<211> LENGTH: 45
<212> TYPE: DNA
<213> ORGANISM: Artificial
<220> FEATURE:
<223> OTHER INFORMATION: Identifier probe

<400> SEQUENCE: 2
ttggtagtga ggcaggtatg aatgccatgt ggacttccag aacac                       45

<210> SEQ ID NO 3
<211> LENGTH: 19
<212> TYPE: DNA
<213> ORGANISM: Artificial
<220> FEATURE:
<223> OTHER INFORMATION: Primer

<400> SEQUENCE: 3
ttggtagtga ggcaggtat                                                     19

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
gtgttctgga agtccacat                                                     19

IDENTIFIER AND NUCLEIC ACID AMPLIFICATION METHOD OF VERIFICATION USING THE SAME

BACKGROUND OF THE INVENTION

1. Field of the Invention

The present invention relates to an identifier that is prepared separately from a specimen and facilitates identification of the specimen when the specimen is subjected to analysis by amplifying a specific region of the specimen, and a primer set using the identifier. The present invention also relates to a specimen storing method, a nucleic acid amplification method and a test method of the results of the amplification, each of these methods using the identifier.

2. Description of the Related Art

As an identification method of a genome DNA sample, known are the identification procedures in which specific repeat sequences such as short tandem repeat sequences and minisatellite sequences are utilized as indicators (Japanese Patent Application Laid-Open No. H06-205700). Additionally, a systematic management method of specimen numbers in specimen processing processes has been actualized by automating the processes (Japanese Patent Application Laid-Open No. H05-288754).

In genetic testing of a disease-related gene and a drug metabolism-related gene, these genes having recently been targeted in pharmacogenomics, a genotyping technique which tests the single nucleotide polymorphisms (SNPs) has attracted attention. In this connection, predominantly used are a method in which a partial sequence containing a polymorphism is amplified, the polymorphism-containing sequence is hybridized with a complementary probe, and whether or not the hybridization is successful is identified, and a method in which genotyping of the polymorphism is carried out by applying a one base extension reaction to the polymorphism site. Accordingly, for the purpose of managing a genome DNA itself as a specimen, it is necessary to always maintain consistent management codes through all the processes from the amplification process of a partial sequence to the final test process for determining the gene. Further, when a part of a DNA specimen is amplified to be tested, the same region is not necessarily amplified from the specimen, sometimes the amplification of the desired part may be unsuccessful, and hence it has been always necessary to examine whether or not the amplification of the desired part is attained.

SUMMARY OF THE INVENTION

When polymorphism-containing fragments from a specimen genome DNA are processed in the subsequent processes (for example, amplification, purification, and detection processes) for the purpose of carrying out genotyping or the like, it is necessary to always identify the original specimen as the fragment supply source. A fragment characteristic to a bacterial genome DNA needs be processed by similar processing processes for the purpose of identifying the bacterial species in the test of a specimen infected with the bacterium; in this case, it is particularly important to determine which the original specimen (infection source) is. For this determination, the identification code of the original specimen must be managed consecutively in every process unit. When two or more specimens are tested at the same time, there is a risk of confusing the identification codes of the original specimens, and sometimes it has been difficult to ensure the reliability of the test on completion of the final process.

As has been described in the section of the background art, it is not practical to manage all the genome base sequences such as partial base sequences to be indicators; even if the management is automated, sequential tests of the specimens themselves are not involved, and hence there has been a problem that the success/failure of the amplification cannot be identified. In general, an identification method of a specimen is one thing, and an identification method of the success/failure of the amplification of a part of a specimen is another. The identification of a specimen in the former method can be carried out by utilizing a unique site of the sequence of the specimen genome DNA as an identification code.

The identification of the partial amplification in the latter method, strictly speaking, requires an amplification test utilizing a standard specimen. A simplified method is carried out to such an extent that whether or not the object of interest is moderately amplified is identified, and the presence/absence of an artificial mistake such that no appropriate primer has been used or no primer has been put in is identified. This identification uses a method based on gel electrophoresis and a method in which labeling is carried out at the time of amplification, and, for example, a fluorescence-labeled product on completion of amplification is identified with a laser. However, each of these methods tests for amplification all the specimens, and hence these methods still have problems for the purpose of improving the test efficiency.

An object of the present invention is to provide an identification technique that can consistently maintain a set of information specifying the specimen through all the processes from the amplification process to the detection process of the specific sequences. Another object of the present invention is to provide a technique that can also identify the completion of a desired amplification in the amplification process.

An identifier of the present invention comprises: a base sequence having a set of information decodable to an individual code corresponding to a specimen composed of a DNA or RNA, and being incorporated into a region amplifiable by using two primers for amplifying the above described specimen.

A primer set of the present invention comprises two primers for amplifying a predetermined region of a specimen composed of a DNA or RNA, wherein the primer set further comprises an identifier having the above described configuration.

A storing method of a DNA or RNA of the present invention stores a specimen comprising a DNA or RNA while managing the specimen with the individual code imparted to the specimen, wherein an identifier having the above described configuration is stored together with the specimen in one and the same container.

A specimen identification kit of the present invention comprises the identifier and the container having an identification code, wherein the individual code is identical with the identification code of the container.

A nucleic acid amplification method of the present invention is a method for amplifying a predetermined region of a specimen imparted with an individual code and composed of a DNA or RNA having a predetermined sequence by using two primers, wherein the method comprises a step of amplifying the predetermined region of the specimen in the concomitant presence of an identifier amplifiable by using above described two primers, and the identifier has a configuration in which a predetermined base sequence located in the region amplifiable by the amplification using the two primers is related to the individual code.

A test method of the amplification results of the present invention comprises a step of detecting the presence/absence of the amplification product derived from the identifier in the amplification products obtained by the above described nucleic acid amplification method, or for detecting and quantitating the above described amplification product.

The identifier according to the present invention has, as a management method of a specimen such as a genome DNA, a base sequence incorporating as a set of decodable information the individual code of the specimen in the region amplifiable by using two primers (universal primers) for the specimen amplification. The identifier is stored as a mixture with the specimen in one and the same container, and when amplification is carried out by using the two primers, the specimen as the origin of the amplification products can be specified by identifying, in the amplification products, the presence of a base sequence containing the set of information contained in the identifier and related to the individual specimen code. Additionally, by attaching the individual specimen code to the container, the container as the supply source of the specimen can be easily specified. In this way, it can be expected that errors of analysis results due to artificial mistakes including mix-up between specimens are reduced to the lowest possible level. The fact that the identifier and the specimen or a part of the specimen can be amplified by using the same universal primers means that whether or not the identifier can be detected makes an indicator to identify the success/failure of the amplification. In the genetic analysis of the specimen, the identification of the fact that the individual code of the specimens and the identifiers can be detected to a satisfactory extent offers an effective method for attaining the reliability of the data when a large number of prepared specimens are associated with the analysis results thereof.

When a specimen is contaminated with another specimen in the processing process of the specimens, the identifiers of both specimens are detected, and hence the fact that a trouble has been caused can be identified at the time of detection, so that the reliability of the analysis data of the specimens can be duly described.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Figures 1, 2:
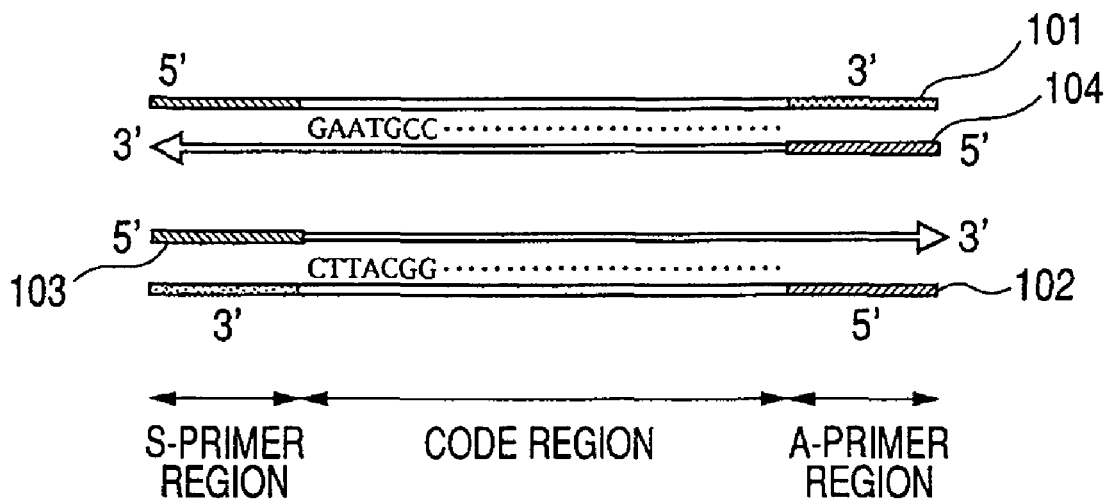
FIG. 1 is a diagram schematically illustrating the structure of an identifier of the present invention and an amplification process thereof.
FIG. 2 is a diagram showing an example of a base sequence into which a set of information about the individual specimen code in the identifier of the present invention is written and the decoded data thereof.

Preferred embodiments of the present invention will now be described in detail in accordance with the accompanying drawings.

The present invention relates to an identifier incorporating an individual specimen code, wherein an identifier and a specimen are mixed together and stored for management in one and the same container, so that the mixture can be subjected to a simultaneous amplification or a simultaneous hybridization to attain the management of the specimen and the processes involved. The base sequence part having a set of decodable information contained in the identifier may be a chemically synthesized sequence, or a sequence obtained by cutting a unique sequence out of an indigenous bacterium genome or a human genome.

Hereinafter, embodiments of the present invention will be described.

First Embodiment

A first embodiment of the present invention is described below with reference to FIGS. 1, 2 and 3. The present embodiment relates to a design of an identifier having a base sequence into which an individual code to identify a specimen is recorded as a set of decodable information. The present embodiment also includes a specimen storing method which stores for management a specimen and an identifier in one and the same container, preferably, as a mixture.

The identifier has a base sequence incorporating as a set of decodable (translatable) information an individual code imparted for identification of a specimen. In other words, by decoding (translating) the base sequence, the individual code of the specimen can be obtained. The identifier has a base sequence defined beforehand in a unique manner in relation to the specimen, in such a way that the identifier is designed so as to be capable of being simultaneously amplified by using the same pair of primers as a pair of primers necessary for the purpose of amplifying the specimen or a part of the specimen. The identifier can identify the individual specimen code by specifying and decoding the set of information, contained in the identifier, about the individual specimen code with the aid of the hybridization between the identifier and a probe, other than the probe for detecting the specimen, for capturing the identifier.

In general, a probe for detecting a specimen and a probe for capturing an identifier are immobilized, on a solid carrier such as glass, plastic and bead, to be used for the above described hybridization. There can also be used a form of microarray in which various probes for detecting specimens and various probes for capturing identifiers are disposed on a substrate.

Methods well known in the art can be utilized for a method for immobilizing each of the probes on the solid carrier, a method for synthesizing each of the probes, and a method for spotting each of the probes on the solid carrier, and preparation apparatuses to be used for these methods. As a detection method of the occurrence/nonoccurrence of a hybridization, there can be used a method selected according to the purpose from the fluorescence method, the radioisotope (RI) method, the electrochemical method, the surface plasmon resonance method, the quartz oscillator method, and other various methods well known in the art. Hereinafter, the embodiment is described on the case where a general fluorescence detection method is used.

FIG. 1 is a diagram schematically illustrating an example of a configuration of an identifier in the central region of which is disposed a base sequence incorporating as a set of decodable information the individual code particularly imparted to a specimen. The identifier 101 has a base sequence "GAATGCC" in the central region thereof, and has binding regions of the amplification primers, namely, the S-Primer region and the A-Primer region in the 3'-end and 5'-end regions of the identifier, respectively. As shown in FIG. 1, a nucleotide chain 102 is a chain complementary to the identifier 101, and the nucleotide chains 103 and 104 each show a nucleotide chain extended with the identifier 101 and 102 as template and the primer as the starting point. In the identifier 101, the central part interposed between the primer regions on the 5'-side and 3'-side is defined as the code region. In the code region, the individual specimen code is incorporated as a set of decodable information.

The complementary chain 104 to the identifier 101 is obtained by annealing an antisense direction primer (A-Primer) in the 3'-end region of the identifier 101, and by extending a nucleotide chain by using the identifier 101 as template with the aid of DNA polymerase. A copy 103 of the identifier 101 is obtained by annealing a sense direction primer (S-Primer) in the 3'-side region of the complementary chain 104, and by extending a nucleotide chain by using the complementary chain 104 as template with the aid of DNA polymerase. Further, a copy 102 of the complementary chain of the identifier 101 is obtained by annealing a primer (A-Primer) on the 3' side of the copy 103, and by extending a nucleotide chain by using the copy 103 as template with the aid of DNA polymerase. By repeating the above described extension reaction using two primers, the copy of the identifier 101 can be obtained in a large amount. In other words, the code region of the identifier 101 is amplified exponentially. This amplification process is a process in which the PCR (polymerase chain reaction) process is applied to the identifier having a set of information decodable to the individual specimen code; thus, when the primer regions are made to coincide with the primer regions for the specimen amplification, the amplification target region of the specimen and the identifier can be simultaneously amplified by the same amplification process.

In the present embodiment, experiments have been carried out by using the specimen and the identifier shown in Table 1.

TABLE 1

| | |
|---|---|
| Example of a specimen sequence CYP2D6 C100T 178 bp | 5'-TTGGTAGTGAGGCAGGTATggggctagaagcactgg tgccctggccgtgatagtggccatcttcctgctcctgg tggacctgatgcaccggcgccaacgctgggctgcacgct acycaccaggcccctgccactgcccgggctgggcaacc tgctgcATGTGGACTTCCAGAACAC-3' (SEQ ID NO. 1) |
| Identifier sequence | 5'-TTGGTAGTGAGGCAGGTATgaatgccATGTGGACTT CCAGAACAC-3' (SEQ ID NO. 2) |
| Forward Primer (S-Primer) | 5'-TTGGTAGTGAGGCAGGTAT-3' (SEQ ID NO. 3) |
| Reverse Primer (A-Primer) | 5'-GTGTTCTGGAAGTCCACAT-3' (SEQ ID NO. 4) |

The primers each having the 5' end labeled with Cy3 have been used. It has been verified that, by using the pair of primers that amplify the specimen, the identifier can also be amplified in such a way that the region containing the central identification code gaatgcc represented with lower case characters can be amplified. In this case, in order to increase the reaction rate, Light Cycler 2.0 (Roche Diagnostics) was used to carry out a 40-cycle PCR (polymerase chain reaction) according to the protocol in Table 2 presented below. As the enzyme (DNA polymerase) and the substrate, Fast Start DNA Master Hybridization Probes (Roche Diagnostics) were used.

TABLE 2

| | Temperature (° C.) | | |
|---|---|---|---|
| | 95 | 60 | 72 |
| Duration time (sec) | 10 | 15 | 7 |

The identifier maintaining the identification code "GAATGCC" as a base sequence in the center, shown in FIG. 1, is configured to be amplifiable by using the same primers as the amplification primers of the specimen.

FIG. 2 shows an example of decoding of the individual specimen code region of an identifier. In this example, for a case where the specimen is imparted with a 14-digit code "10111100100101" as the individual code of the specimen, there is presented a case where is applied a simple decode scheme in which the bases A (adenine), G (guanine), C (cytosine) and T (thymine) are replaced with the 2-bit codes, 11, 10, 01, and 00, respectively, and the individual specimen code is replaced, as a set of decodable information, with a base sequence. In other words, when the sequence "GAATGCC" disposed in the code region of the identifier 101 is identified in an amplification product obtained by the above described amplification, the decoding of the base sequence makes recognizable the individual code "10111100100101" particularly imparted to the specimen, and thus a successful amplification of the identifier 101 can be identified. The individual specimen code is not limited to the above described string of digits, but can adopt a character string composed of one or more selected from digits, characters (Japanese characters, alphabetical characters and the like) and symbols.

With a base length of the identifier 101 as long as 50 bp, such length means a possibility of defining a 100 bit individual code, and a redundant coding of the individual code for specimen identification is also technically feasible. Examples of the applicable coding technique include a technique related to the encryption of computer codes for security enhancement and a technique related to code shrinkage for compressing data for images and the like.

Figure 3:
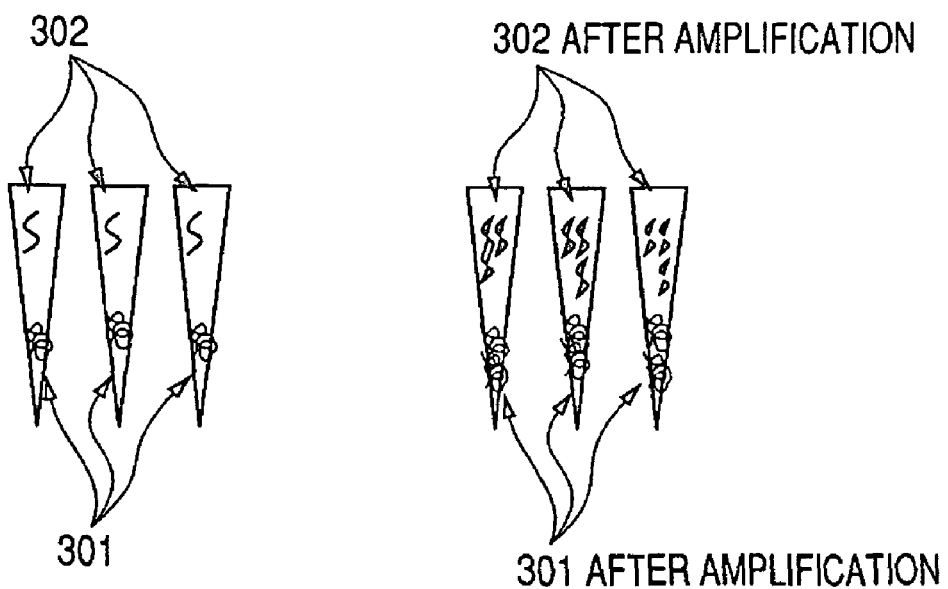
FIG. 3 is diagram showing an example of the application of the identifier of the present invention.

FIG. 3 shows an example of the application of the identifier having a set of information about an individual specimen code. A specimen and an identifier having a set of information about the individual code of the specimen are mixed together and put in a container for storing a specimen sample, in particular here, a container such as a microtube or the wells of a microtiter plate. The identifier may be beforehand placed in the container; alternatively, the identifier may be placed in the container simultaneously when the specimen is placed, and then the identifier and the specimen may be mixed together. It is useful to offer the specimen and the identifier as a kit that enables both storage and identification.

Reliable storage and management are made possible by imparting the individual specimen code to the container when the specimen and the identifier are mixed together. For example, the individual specimen code is recorded, on the container in which the specimen is placed, in various forms such as a label, a barcode, a two-dimensional code. Additionally, the identification code of the container may also be coded in the same manner as in the individual specimen code.

Then, in the container specified by the individual specimen code, prepared is a mixture composed of the identifier having a set of information about the individual specimen code and the specimen having the individual code. By recording the interrelation between the specimen and the container code, the specification of the container of the offering source and the identification of which specimen is contained in the mixture can be carried out without fail. For example, even when the mixture is separated away from the initial container in various subsequent processes, as long as the mixture is processed as it is a mixture, the management of the specimen can be carried out without fail with the aid of the individual code imparted to the specimen by correlating the mixture with the container of the offering source. In this connection, it is necessary to select the sequence of the identifier for the purpose of avoiding the case where the specimen and the identifier are annealed in a specific manner to affect the subsequent reactions. In the initial state, the specimen 301 and the identifier 302 shown in FIG. 3 are stored in a state of being mixed together. For the purpose of carrying out the genetic test of the specimen, the specimen or a partial sequence of the specimen is amplified. As primers for amplification, there are used universal primers which can be used in common for the amplification of the amplification site of the specimen 301 and the amplification of the identifier. In this way, when there occurs a mistake that no primer has been put in or a problem in the amplification process, such a mistake or a problem can be confirmed on the basis of whether or not the identifier can be detected. In other words, the identifier can be used as a indicator for testing the amplification.

The detection of the identifier can be easily carried out by applying the hybridization with the complementary chain probe thereof because of the beforehand designed sequence of the identifier. When two or more specimens are tested, the arrangement and immobilization of the probes for capturing the identifiers corresponding to the respective specimens on a solid carrier can improve the test efficiency. When a test is carried out using identifiers corresponding to a large number of specimens, a probe immobilization form such as a microarray is preferable.

Figure 4:
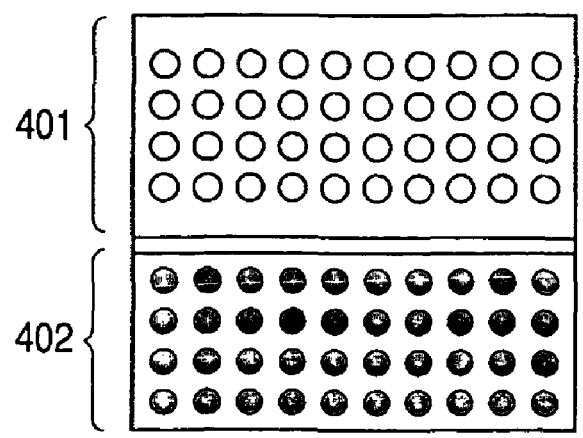
FIG. 4 is a schematic plan view of an example of a solid carrier which carries out the hybridization with the identifier of the present invention and a specimen (or a part thereof) wherein a probe on the detection side is mounted on the solid carrier.

The region where the probes for capturing the identifiers are immobilized may be arranged on a carrier to be used for the genetic test of the specimens. In this case, because the specimens and the test results thereof can be detected together with the individual codes of the identifiers on the same carrier, there can be expected beneficial effects of avoiding human errors such as mix-up between specimens and mistakes in registration of analysis results. FIG. 4 schematically shows a solid carrier as a microarray, which comprises an analysis area 401 where are arranged probes for testing specimens and an identification code area 402 where probes for capturing identifiers containing a set of information about the individual codes of the specimens are arranged in a number as many as the number of the specimens being managed. These two areas prepared on two separate solid carriers fall within the scope of the present invention; however, needless to say, a design to arrange these two areas on one carrier is preferable for the purpose of managing the specimen data.

In the identification code area 402 arranged on the microarray, the probes for capturing the identifiers the number of which corresponds to the number of the specimens as the test objects are disposed each alone. The state in which the identifiers (amplification products) are hybridized with the probes for capturing the identifiers is detected by utilizing fluorescence labels. The fluorescence labels are set to be incorporated into the amplification products when the identifiers are amplified. When the identifiers are bonded to the probes, immobilized in the identification code area 402, for capturing the identifiers, fluorescence can be obtained by irradiating the object area with an excitation light. The fluorescence is detected with a fluorescence detector, a fluorescence spot analyzer or the like.

The specimens and the identifiers amplified in the present embodiment are made to be hybridized with the above described microarray, and thereafter are subjected to the detection of the Cy3-labeled specimens and the Cy3-labeled identifiers by using GenePix4000 (Inter Medical Co., Ltd.). Judgment is made as to whether or not the spots concerned in the analysis area 401 and the identification code area 402 can be detected, depending on whether or not the specimens are mixed.

TABLE 3

|  | Probe for capturing identifier A | Probe for capturing identifier B |
|---|---|---|
| (1) No amplification candidate | − | − |
| (2) Only amplification candidate A | + | − |
| (3) Only amplification candidate B | − | + |
| (4) Amplification candidates A and B | + | + |

+ Brightness found, − No brightness

An identifier is an oligonucleotide synthesized as described above, and brightness can be detected in the presence of a pair of amplification primers, an enzyme DNA polymerase and a substrate as shown in Table 3. The brightness is independent of the amplification state of the specimen. This can be verified from the brightness of the probe for capturing the identifier located in the identification code area 402. For the case of "(2) only amplification candidate A" in Table 3, the analysis area is assumed to be in a condition as shown in Table 4.

TABLE 4

|  | Probe for capturing amplification product A | Probe for capturing amplification product B |
|---|---|---|
| Analysis area example 1 | − | − |
| Analysis area example 2 | + | − |
| Analysis area example 3 | − | + |
| Analysis area example 4 | + | + |

+ Brightness found, − No brightness

The example 1 shows that the amplification is unsuccessful because the identifier can be identified but no amplification product can be identified. The example 2 shows that the amplification product A can be identified as expected. The examples 3 and 4 show that the contamination due to the amplification product B occurs.

From the sequence of the probe, immobilized at the position where fluorescence is detected, for capturing an identifier, the sequence of the identifier bonded to the position is specified, and the individual code, contained in the amplification product, of the specimen can be decoded. In other words, from fluorescence measurement, the individual code of the specimen is displayed, and thus the fact that the amplification of the specimen is free from any problems can be notified. The detection and analysis of the fluorescence in the identification code area and the notification processing of the results can be controlled by the program codes recorded on the ROM/RAM of the detection apparatus and the image analyzer. Further, by measuring the amplification amount of the identifier with the aid of the fluorescence intensity or the like, the amplification amount of the specimen can also be estimated.

The above described judgment can also be carried by an information processing apparatus mounted with a microprocessor capable of taking in an image as follows: the whole identification code area 402 being in a sate capable of obtaining fluorescence by excitation light irradiation is taken, as a fluorescence image, in the information processing apparatus, and the image data thus obtained is processed by a program installed beforehand. In this case, the program codes may be stored in external recording media such as a hard disk, a flush memory, a CD, a DVD and a FD. Errors found on completion of the analysis may be output, as the code display of the specimen, for example, onto a PC display to promote awareness in terms of specimen sample preparation failure, illegibility of results or the like. The present invention as a management system of a specimen may adopt the detected data of the identifier of the specimen as an ID code of the specimen. In other words, when the analysis data of the specimen are made to include the analysis results of the identifier, the analysis data of the specimen is linked with the specimen ID and thus, the analysis data can be directly recorded, for example, on the data base system; the above inclusion of the analysis results of the identifier also serves for automation of a successive series of the processes of the specimen preparation, amplification, purification, analysis, extraction of the results and registration of the analysis data. In this case, there can be constructed a system in which human errors such as the mistakes in specimen registration and preparation can be reduced to the lowest possible level.

In the present embodiment, there can be provided a specimen test kit in which in a container with the individual specimen data attached thereon, the identifier having the set of information about the individual data is placed. Further, there can also construct a library of the specimens managed with the individual codes by mixing the identifier and the specimens corresponding thereto in the container in this kit. Further, this kit may be added with a solid carrier for detecting the identifiers on which carrier the probes for capturing the identifiers are immobilized. Further, a solid carrier on which the specimen test probe is immobilized may be provided, as a separate article or as an integrated article.

The above described method for carrying out the identification and the amplification test of the specimens by using the identifiers can also be utilized for checking the quality of a large number of stored specimens such as a genome library. For example, the fact that specimens are stored in satisfactory conditions without being contaminated with foreign specimens can be verified by periodically sampling a part of the specimens each being in a state of being mixed with an identifier, by amplifying the sampled specimens, and by obtaining such a result that only the amplified products derived from the identifiers can be detected.

Second Embodiment

A second embodiment of the present invention is described below with reference to FIG. 5. The present embodiment relates to an identifier design carried out by extracting a base sequence unique (intrinsic) to a specimen and by adopting the base sequence as an individual code of the specimen.

Examples of the base sequence unique to a specimen include specific repeated sequences found in a genome such as a short tandem repeat and a minisatellite. The genome identification methods utilizing these sets of information as sample codes are well known in the art (Japanese Patent Application Laid-Open No. H06-205700). In the present embodiment, described is a designing of an identifier to be carried out by extracting a repeated region or a polymorphism region of a genome from a specimen, and by making the extracted region undergo ligation with a probe having the sequence corresponding to the amplification primers.

Figure 5:
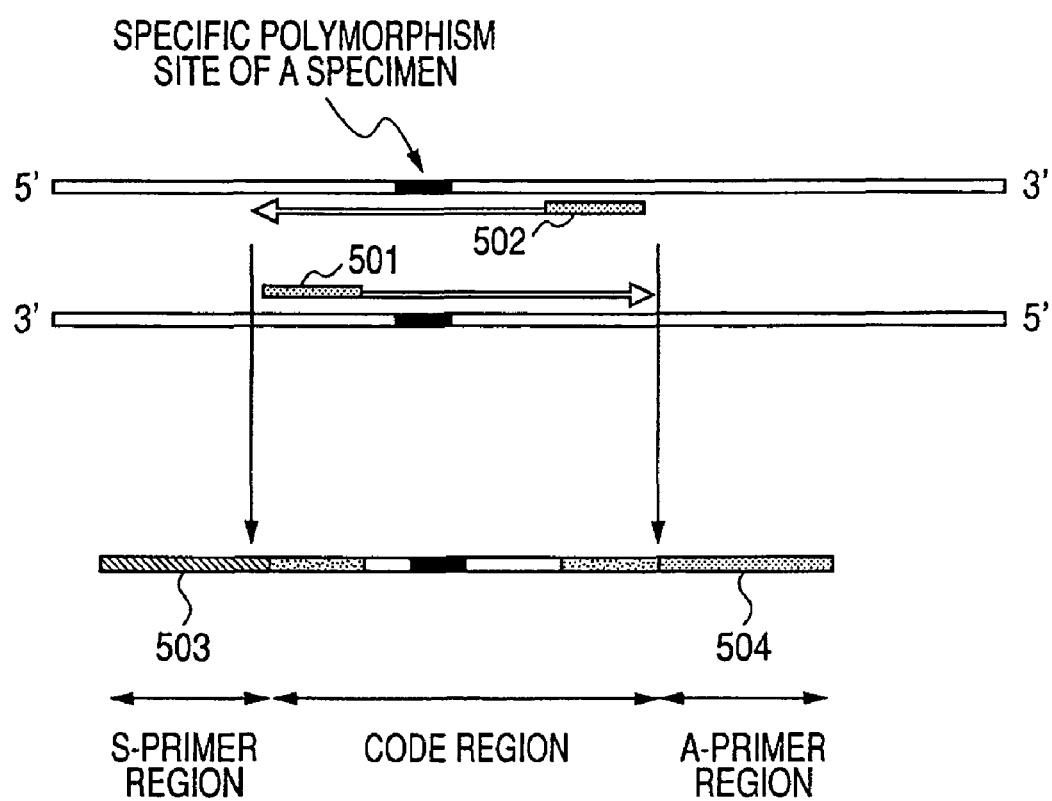
FIG. 5 is a diagram schematically showing the process for extracting a polymorphism site of a genome in a second embodiment of the present invention.

FIG. 5 schematically shows the process for synthesizing an identifier by extracting a polymorphism site of a specimen genome. In FIG. 5, reference numeral 501 denotes a primer (sense direction primer) for extracting and amplifying the polymorphism site of the specimen, and reference numeral 502 denotes a primer (antisense direction primer) region for extracting and amplifying the polymorphism site of the specimen. Additionally, reference numeral 503 denotes a primer (sense direction primer) region for amplifying an identifier, and reference numeral 504 denotes a primer (antisense direction primer) for amplifying an identifier. Here, the genome may be the human genome of the specimen itself or the genome of an indigenous bacterium. Here is presented a process for synthesizing an identifier by extracting, after amplification, a unique polymorphism site of a human genome specimen, and by ligating to the both ends of the extracted region adapters each having the sequence to be a complementary chain to the primer for analysis of the specimen. In this case, a particular, specific optional sequence cannot be selected as the region having a set of information about the individual code of the specimen, but there is an advantage that a region not in cross sequence with the analysis region of the specimen can be intentionally selected. Two or more unique sequences are extracted as the polymorphism sites, and two or more corresponding identifiers may be prepared.

In the case of the present embodiment, an identifier is synthesized by selecting, at every synthesis, a sequence usable as the individual specimen code from the polymorphism-containing region of the specimen, and hence the individual specimen code cannot be fixed beforehand. Accordingly, it is necessary to add to the library the on-the-microarray probe for capturing an identifier, every time when the identifier is synthesized, wherein the on-the-microarray probe for capturing the identifier is hybridized with the identifier.

As for the identifier to be utilized in the present invention, two or more different identifiers may be used for one specimen as long as these identifiers are made to correspond to the specimen in a satisfactory manner. An increased number of identifiers sometimes makes it possible to carry out a more accurate judgment.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-266021, filed Sep. 13, 2005, which is hereby incorporated by reference herein in its entirety.

What is claimed is:

1. A nucleic acid amplification method in which a predetermined region of a specimen imparted with an individual code and composed of a DNA or RNA having a predetermined sequence is amplified by using two primers, comprising:
  mixing the specimen with an identifier probe that is not obtained from the specimen, the identifier probe comprising a base sequence having a set of information decodable to the individual code, the base sequence being incorporated into a region of the identifier probe amplifiable by using the two primers; and
  amplifying the predetermined region of the specimen and the region of the identifier probe by using the two primers, while the specimen is in the concomitant presence of the identifier probe.

2. A test method of the amplification results, comprising a step of detecting the presence/absence of an amplification product derived from the identifier probe in the amplification products obtained by the nucleic acid amplification method according to claim 1.

3. The test method according to claim 2, wherein detection of the amplification product derived from the identifier probe is carried out by making the amplification product incorporate a label and by detecting with the aid of the label hybridization of the amplification product to a probe for capturing the identifier probe having a complementary sequence specifically bonding to the amplification product.

4. The test method according to claim 2, wherein in the case where when hybridization between the amplification product derived from the identifier probe and the probe for capturing the identifier probe is not detected, a set of error information indicating failure of amplification of the specimen is displayed.

5. The test method according to claim 2, wherein
  there are two or more sets each of which is composed of the specimen and an identifier probe corresponding to the specimen;
  for every identifier probe, a probe for capturing the identifier probe is prepared;

then the amplification product obtained from one specimen and the identifier probe corresponding thereto is applied to the respective probes for capturing identifier probes; and when reactions with at least two probes for capturing an identifier probe are found to occur, there is formed a set of error information that indicates the amplification error or the specimen contamination.

6. The test method according to claim 2, wherein the probe for capturing the identifier probe is immobilized on a solid carrier and is made to be reacted with the amplification product derived from the identifier probe.

7. The test method according to claim 6, wherein an identification area in which the probe for capturing the identifier probe is immobilized and a detection area in which a probe for analyzing the specimen is immobilized are disposed in a manner partitioned from each other on the solid carrier.

8. The test method according to claim 7, wherein
the occurrence/nonoccurrence of hybridization in the identification area is taken in as an image;
the occurrence/nonoccurrence of hybridization in the detection area is taken in as an image; and
the individual code of the specimen and the analysis data of the specimen are processed in an interrelated manner on the basis of these images.

9. The test method according to claim 2, wherein the amplification product is detected and quantitated.

10. The method according to claim 1, wherein the specimen and the identifier probe are amplified simultaneously in the step of amplifying.

11. A test method of the amplification results, comprising a step of detecting the presence/absence of an amplification product derived from the identifier probe in the amplification products obtained by the nucleic acid amplification method according to claim 10.

* * * * *